US010465155B2

(12) United States Patent
Kim

(10) Patent No.: US 10,465,155 B2
(45) Date of Patent: Nov. 5, 2019

(54) NON-LINEAR FLOW PATH DEVICES AND METHODS FOR CELL CULTURE

(71) Applicant: Board of Regents, The University of Texas System, Austin, TX (US)

(72) Inventor: Hyun Jung Kim, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 152 days.

(21) Appl. No.: 15/231,318

(22) Filed: Aug. 8, 2016

(65) Prior Publication Data

US 2017/0088807 A1   Mar. 30, 2017

Related U.S. Application Data

(60) Provisional application No. 62/203,017, filed on Aug. 10, 2015.

(51) Int. Cl.
*C12M 1/00*  (2006.01)
*C12M 3/06*  (2006.01)
*C12M 1/42*  (2006.01)

(52) U.S. Cl.
CPC ............ *C12M 23/16* (2013.01); *C12M 23/26* (2013.01); *C12M 23/34* (2013.01); *C12M 27/20* (2013.01); *C12M 29/14* (2013.01); *C12M 35/04* (2013.01)

(58) Field of Classification Search
CPC ...... C12M 23/08; C12M 23/16; C12M 23/26; C12M 23/34; C12M 23/38; C12M 21/08; C12M 25/02; C12M 27/02; C12M 29/04; C12M 29/06; C12M 27/20; C12M 29/14; C12M 35/04

USPC ............................... 435/289.1, 297.2, 305.2
See application file for complete search history.

(56) References Cited

U.S. PATENT DOCUMENTS

| 8,642,326 | B1* | 2/2014 | Schaefer | A01G 33/00 435/292.1 |
| 2007/0141555 | A1* | 6/2007 | Deutsch | C12M 29/04 435/4 |
| 2013/0115695 | A1* | 5/2013 | Schulz | C12N 5/0606 435/366 |
| 2014/0038279 | A1* | 2/2014 | Ingber | C12M 25/02 435/297.2 |

FOREIGN PATENT DOCUMENTS

| WO | WO 2010/009307 | 1/2010 | |
| WO | WO-2010009307 A2 * | 1/2010 | .......... B01L 3/50273 |

(Continued)

OTHER PUBLICATIONS

Benam, Kambez H., et al. "Engineered in vitro disease models." *Annual Review of Pathology: Mechanisms of Disease* 10 (2015): 195-262.

(Continued)

*Primary Examiner* — Liban M Hassan
(74) *Attorney, Agent, or Firm* — Parker Highlander PLLC

(57) ABSTRACT

Devices and methods cell culture are disclosed herein. In particular embodiments, the cell culture devices include multi-channel devices with a non-linear flow path that recapitulates the three-dimensional microarchitecture and physiological organ-level functions of human organs with cellular and molecular resolution.

12 Claims, 9 Drawing Sheets

(56) References Cited

FOREIGN PATENT DOCUMENTS

| WO | WO 2012/118799 | 9/2012 |
|----|----------------|--------|
| WO | WO 2013/086502 | 6/2013 |

OTHER PUBLICATIONS

Choi, Jin-Ha, et al. "Priming nanoparticle-guided diagnostics and therapeutics towards human organs-on-chips microphysiological system." Nano Convergence 3.1 (2016): 24.

Huh, Dongeun, et al. "Microengineered physiological biomimicry: organs-on-chips." *Lab on a chip* 12.12 (2012): 2156-2164.

Huh, Dongeun, et al. "Microfabrication of human organs-on-chips." *Nature protocols* 8.11 (2013): 2135-2157.

Kang, Tae Hyun, and Hyun Jung Kim. "Farewell to Animal Testing: Innovations on Human Intestinal Microphysiological Systems," *Micromachines* 7.7 (2016): 107.

Kim, Hyun Jung, and Donald E. Ingber. "Gut-on-a-Chip microenvironment induces human intestinal cells to undergo villus differentiation." *Integrative Biology* 5.9 (2013): 1130-1140.

Kim, Hyun Jung, et al. "Co-culture of living microbiome with microengineered human intestinal villi in a gut-on-a-chip microfluidic device." JoVE (Journal of Visualized Experiments) 114 (2016): e54344-e54344.

Kim, Hyun Jung, et al. "Contributions of microbiome and mechanical deformation to intestinal bacterial overgrowth and inflammation in a human gut-on-a-chip." *Proceedings of the National Academy of Sciences* 113.1 (2016): E7-E15.

Kim, Hyun Jung, et al. "Human gut-on-a-chip inhabited by microbial flora that experiences intestinal peristalsis-like motions and flow." *Lab on a Chip* 12.12 (2012): 2165-2174.

Lee, Jaewon, Jin-Ha Choi, and Hyun Jung Kim, "Human gut-on-a-chip technology: will this revolutionize our understanding of IBD and future treatments?." (2016): 883-885.

Odijk et al. "Measuring direct current trans-epithelial electrical resistance in organ-on-a-chip microsystems." *Lab on a Chip* 15.3 (2015): 745-752.

Park, Gun-Seok, et al. "Emulating Host-Microbiome Ecosystem of Human Gastrointestinal Tract in Vitro." Stem cell reviews (2017).

\* cited by examiner

NON-LINEAR FLOW PATH DEVICES AND METHODS FOR CELL CULTURE

CROSS-REFERENCE TO RELATED APPLICATIONS

This application claims priority to U.S. Provisional Patent Application Ser. No. 62/203,017, entitled "Non-Linear Flow Path Devices and Methods for Cell Culture" and filed Aug. 10, 2015, the contents of which are incorporated herein by reference.

BACKGROUND OF THE INVENTION

1. Field of the Invention

Embodiments of the present invention relate generally to the field of cell culture devices and methods. Particular embodiments concern multi-channel cell culture methods and devices with a non-linear flow path that recapitulates the three-dimensional microarchitecture and physiological organ-level functions of human organs with cellular and molecular resolution.

2. Description of Related Art

Existing devices and methods include shortcomings that affect the ability to efficiently and effectively culture cells in an environment that replicates the unique physical and physiological microenvironments of in vivo human organs. For example, existing devices and methods can present difficulties in culturing multiple types of cells within a single device to introduce sufficient time frame for cell-cell, cell-microbe, cell-extracellular matrix (ECM), cell-exogenous compound (e.g. toxin), or cell-secretome (e.g. microbial metabolites, cytokines, chemokines) communications depending on the user demands because the residence time of culture medium or fluid passing through the microdevice is extremely limited in few minutes. In addition, existing devices and systems can present challenges in independently manipulating the micro physiological conditioning of individual device compartments at different levels of stimulation, as well as the spatiotemporal addition of antigens or different density of cells. The description of issues with existing devices and methods disclosed herein is merely exemplary and not intended to indicate an exhaustive listing of all such issues.

SUMMARY OF THE INVENTION

Embodiments of the present disclosure comprise a biomimetic microfluidic device configured to recapitulate the three-dimensional microarchitecture and physiological organ-level functions of human organs with cellular and molecular resolution.

Particular embodiments comprise a microfluidic device consisting of multiple parallel juxtaposed cell microchannels separated by elastic porous ECM-coated basement membranes for recreating compartments mimicking a lumen (a top microchannel), a mesenchyme (a middle microchannel), and a capillary vasculature (a bottom microchannel).

As described herein, exemplary embodiments comprise features configured to emulate unique physical microenvironments of in vivo human organs, including for example, an externally-exposed lumen side, a capillary blood vessel, and an interstitial mesenchymal space.

Exemplary embodiments of the present disclosure provide significant advances over existing devices. For example, certain embodiments provide a triple-layered microenvironment to mimic organ-level physiological responses occurring in the lumen-mesenchyme-vasculature transmural tissue interface in the human body. These multiple compartments can provide spatial microarchitecture to culture multiple human and microbial cells. In addition, other advances include widened microchannel width and height, multiple baffles to induce dynamic mixing of nutrients, exogenous compounds, and microbial cells, and extended residence time of fluid inside the device. In addition, pneumatic mechanoactuation system can provide bi-directional mechanical deformation of compression and tension to cells and microbes grown in the central cell chambers. In certain embodiments, patient samples (e.g. cells, microbiota, serum, blood, etc.) may be obtained (e.g. via biopsy or stool sample) and placed on the device.

Certain embodiments include a cell culture device comprising: a body having a central channel disposed therein; and a first membrane positioned within the central channel and along a plane, the membrane configured to separate the central channel to form a first central microchannel and a second central microchannel, where: a portion of the first membrane is porous and flexible; a first fluid is directed through the first central microchannel and a second fluid is directed through the second central microchannel; the first membrane is configured to support adhesion of a plurality of living cells; and the first central microchannel comprises a non-linear flow path for the first fluid. In particular embodiments, the first central microchannel comprises a plurality of baffles. In some embodiments, the plurality of baffles is coupled to opposite sides of the first central microchannel. Specific embodiments further comprise a first chamber and a second chamber, wherein the central channel and the first membrane are disposed between the first chamber and the second chamber.

In certain embodiments, the first chamber and the second chamber are configured to exert a compression force on the first membrane. In particular embodiments, a pressure within the first chamber and the second chamber can be increased to exert a compression force on the first membrane. In some embodiments, the first chamber and the second chamber are configured to exert a tension force on the first membrane. In specific embodiments, a pressure within the first chamber and the second chamber can be decreased to exert a tension force on the first membrane. Certain embodiments further comprise a third chamber, wherein the first membrane is disposed between the third chamber and the second central microchannel. In particular embodiments, the third chamber is an anaerobic gas chamber and the first and second chambers are pneumatic chambers. In some embodiments, the first membrane is coated with a molecule that supports adhesion of a plurality of living cells. In specific embodiments, living cells are disposed within the central channel. In certain embodiments, the living cells are epithelial cells, and in particular embodiments the living cells are endothelial cells. In some embodiments, epithelial and endothelial cells are coupled to the first membrane. Specific embodiments further comprise a second membrane positioned within the central channel and along a plane, the second membrane configured to separate the central channel to form a third central microchannel.

In certain embodiments, the first, second and third central microchannels are configured to emulate the structure and physiological functions of a human organ. In particular embodiments, the third central microchannel contains a hydrogel. In some embodiments, the hydrogel has a physiological stiffness equivalent to a connective tissue layer. In specific embodiments, the third central microchannel comprises a second non-linear flow path. In certain embodiments, the third central microchannel comprises a second plurality of baffles.

Particular embodiments include a method of culturing cells, the method comprising: directing a first fluid in a non-linear flow path through a first microchannel of a cell-culture device; and directing a second fluid through a second microchannel of the cell-culture device, where: a first membrane is positioned between the first and second microchannel; a portion of the first membrane is porous and flexible; and the first fluid comprises a plurality of living cells. In some embodiments, the first membrane is configured to support adhesion of the plurality of living cells. In specific embodiments, the first microchannel comprises a plurality of baffles. In certain embodiments, the plurality of baffles are coupled to opposite sides of the first microchannel. In particular embodiments, the first and second microchannels are disposed between a first chamber and a second chamber and wherein the method further comprises: altering the pressure within the first and second chambers to exert a force on the first membrane and the first and second microchannels. In some embodiments, the pressure within the first and second chambers is altered to exert a compression force on the first membrane and the first and second microchannels. In specific embodiments, the pressure within the first and second chambers is altered to exert a compression force on the first membrane and the first and second microchannels.

Certain embodiments further comprise a third chamber, wherein the first membrane is disposed between the third chamber and the second central microchannel. In particular embodiments, the third chamber is an anaerobic gas chamber and the first and second chambers are pneumatic chambers. In some embodiments, the living cells are epithelial cells, and in specific embodiments the living cells are endothelial cells.

In certain embodiments, the cell culture device further comprises a second membrane and a third central microchannel disposed between the first microchannel and the second microchannel. Particular embodiments further comprise controlling the flow of the first and second fluids and the exerting forces on the first and second membranes to emulate the structure and physiological functions of a human organ. In some embodiments, the first microchannel, second microchannel, or the third microchannel comprises a hydrogel. In specific embodiments, the hydrogel has a physiological stiffness equivalent to a connective tissue layer. In certain embodiments, the third microchannel comprises a second non-linear flow path. In particular embodiments, the third microchannel comprises a second plurality of baffles.

It is understood that other embodiments according to the present disclosure may comprise configurations different from those shown and described herein. For example, other embodiments may comprise only a single membrane that divides a central microchannel into two separate microchannels rather than two (or more) membranes that divide a central microchannel into three (or more) central microchannels.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
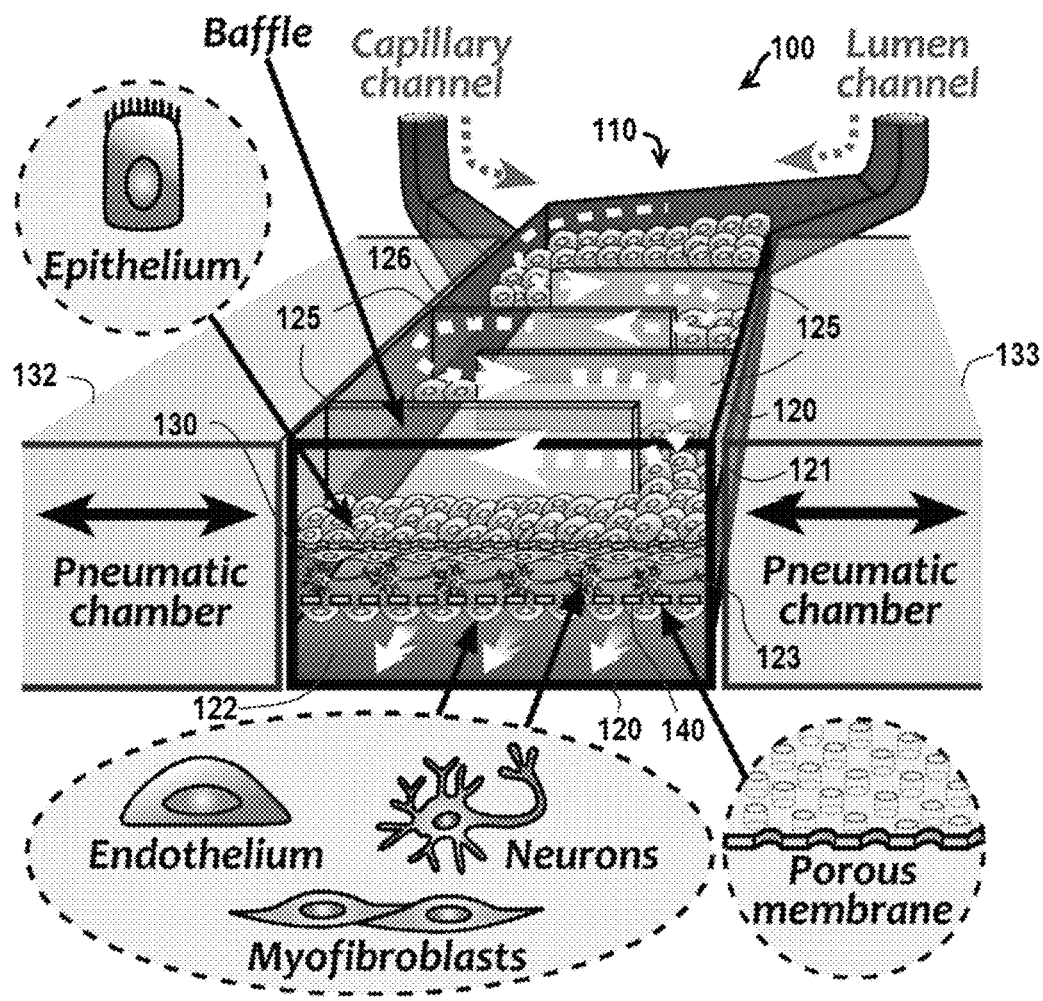
FIG. 1 is a perspective view of a cell culture device according to exemplary embodiments of the present disclosure.
Figure 2:
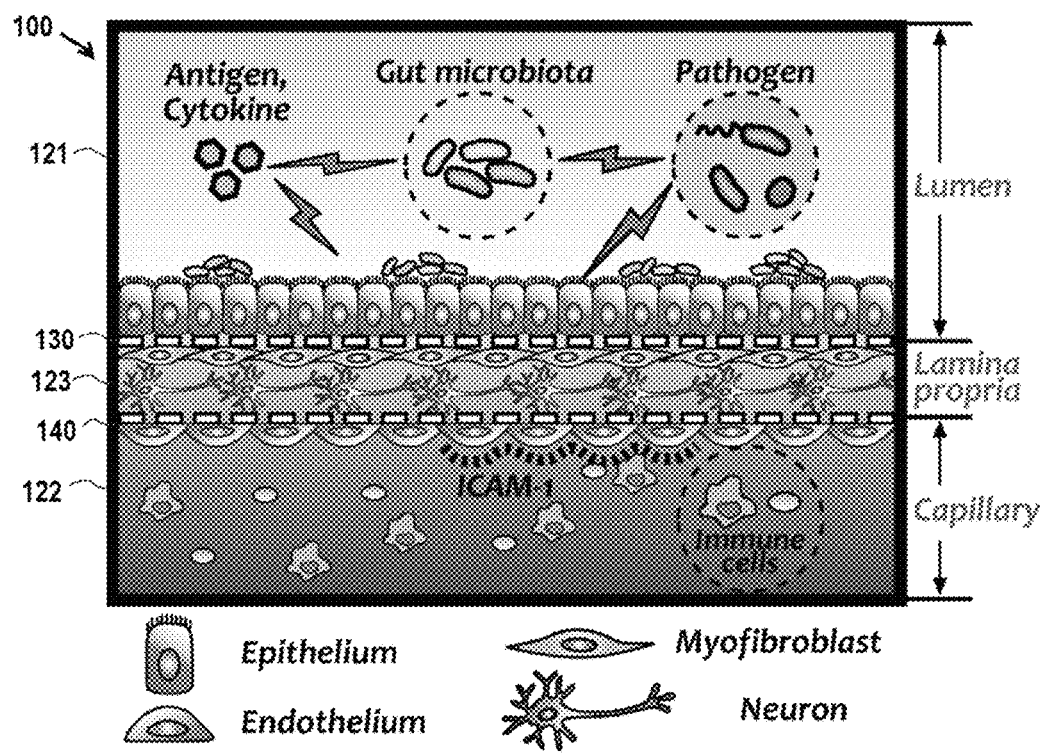
FIG. 2 is a section view of the embodiment of FIG. 1

Referring initially to FIGS. 1 and 2, perspective and cross-section views are illustrated of an exemplary embodiment of a cell culture device 100 according to the present disclosure. In this embodiment, cell culture device 100 comprises a body 110 having a central microchannel 120 disposed therein. A first membrane 130 is positioned within central microchannel 120 along a plane and is configured to separate central microchannel 120 into a first central microchannel 121 and a second central microchannel 122. In this embodiments, a second membrane 140 is also positioned within central microchannel 120 and configured to further separate central microchannel 120 into a third central microchannel 123. In exemplary embodiments, first membrane 130 and second membrane 140 are at least partially porous and at least partially flexible (e.g. at least portions of first membrane 130 and second membrane 140 are porous and at least portions of first membrane 130 and second membrane 140 are flexible). In addition, first membrane 130 and second membrane 140 are configured to support adhesion of a plurality of living cells. In particular embodiments, first membrane 130 and second membrane 140 may include attachment extracellular matrix molecules that support adhesion of living cells. In the embodiment shown in FIG. 1, cell culture device 100 comprises chambers 132 and 133 disposed on each side of first, second and third central microchannels 121, 122 and 123.

During operation, first membrane 130 and second membrane 140 are configured to allow contents of the microchannels to move from one side of each membrane to the opposite side of the membrane. In addition, first membrane 130 and second membrane 140 are configured are configured to flex or deflect from a planar shape to a non-planar shape when exposed to vacuum-driven cyclic mechanical forces during operation. The flexible nature of first membrane 130 and second membrane 140 also allows for the membranes to return back to a planar configuration when they are not being exposed to mechanical forces. As explained in more detail below, the pressure within chambers 132 and 133 can be varied to alter the mechanical forces applied to first membrane 130 and second membrane 140.

In particular embodiments it is possible to deposit different type of cells within the microchannels for mimicking multi-layered tissue interfaces. For example, during operation of exemplary embodiments, first central microchannel 121 can mimic a lumen exposed to the outside of the body, second central microchannel 122 can mimic a connective tissue emulating mesenchyme, and third central microchannel 123 can mimic a capillary vasculature. On the surface of second membrane 140 in the lumen (e.g. first central microchannel 121) and the capillary microchannel (e.g. third central microchannel 123), epithelial and endothelial cells can be simultaneously cultured to form a transmural tissue-tissue interface. In the mesenchyme (e.g. second central microchannel 122), myofibroblasts, muscle cells, resident immune cells (e.g. macrophages, dendritic cells) or other mesenchymal cells including neuron cells can be co-cultured in hydrogel that has a physiological stiffness and resilience for emulating a connective tissue layer between the lumen and blood vessels.

In this multi-layered lumen-mesenchyme-capillary interface, one can adapt various human cells as the component of each layer to mimic morphological and functional aspects of the microenvironment of human organs. In addition, by actuating the cell channels with cyclic motions of compression and tension in the hollow chambers as well as trickling fluid flow, one can apply physiological mechanical deformations and fluid shear stress if this physical dynamics is required in the device.

FIG. 2 provides a vertical cross-section view of cell culture device 100 as a representative example of an intestinal microenvironment in a part of small intestinal villi. This multi-layered structure allows culturing multiple types of intestinal cells in each layer depending on the user demands. In addition, it is possible to independently manipulate the micro physiological conditioning to each compartment at different levels of stimulation, spatiotemporal addition of antigens, or different density of cells. Features of exemplary embodiments can demonstrate interactions in the tissue-tissue interface (e.g. transmural transport from the lumen to capillary blood vessel via mesenchymal diffusion, infection of microbial cells from the lumen to the abluminal compartment, migration of immune cells from blood vessel to mesenchyme or epithelial layer). Accordingly, exemplary embodiments can demonstrate organ-level in vivo relevant responses, which are distinct from tissue-specific responses that can be predominantly achieved by the previous two-dimensional models that have been performed in a static Transwell system or in a plastic dish.

Figure 3:
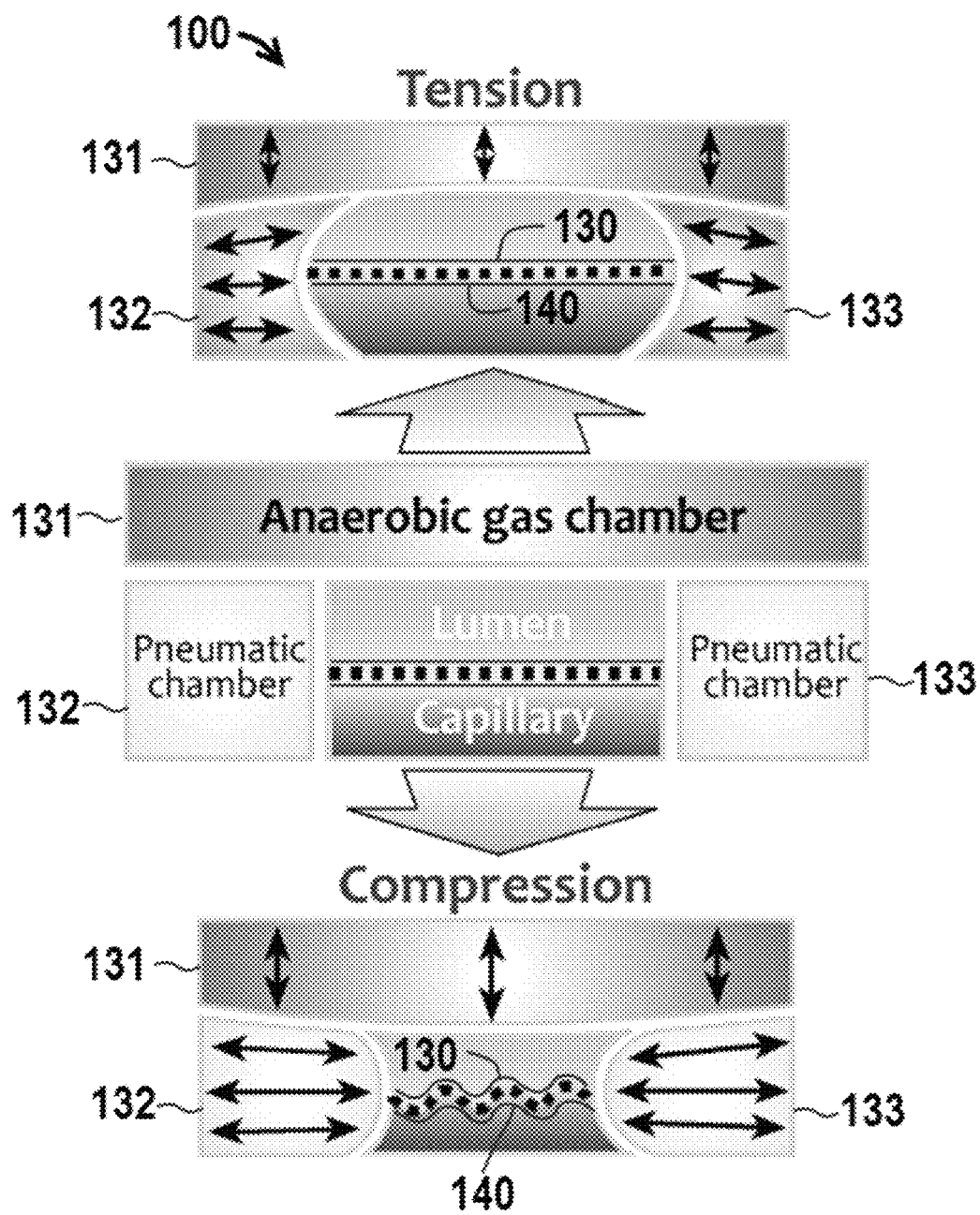
FIG. 3 is a schematic view of the embodiment of FIG. 1 during different states of operation.

Referring now to FIG. 3, a schematic of a cell culture device 100 is shown in various stages of mechanoactuation. For purposes of clarity, not all components are labeled in FIG. 3. Mechanoactuation can be used to exert bidirectional physical mechanical forces to cells cultured within cell culture device 100. In particular embodiments, cyclic mechanical motions of tension (shown at the top of FIG. 3) and compression (shown at the bottom of FIG. 3) are driven by sequentially repeated pneumatic modulations of chambers 131, 132 and 133. For example, a vacuum pump and a compressor can be incorporated in a computer-controlled module that sequentially change positive and negative pneumatic actuation to exert compression and tension deformations. The pressure within chambers 131, 132 and 133 may be reduced (e.g. the chambers can placed under vacuum) to exert tension forces on first membrane 130 and second membrane 140. In addition, the pressure within chambers 131, 132 and 133 may be increased to exert compression forces on first membrane 130 and second membrane 140. Such actuation can present physiologically relevant mechanical dynamics for emulating the dynamics of living tissues, as well as organs of a human body.

Referring back now to FIG. 1, a plurality of baffles 125 are located within first central microchannel 121. It is understood that other embodiments may include additional baffles in other central microchannels, and/or a different configuration of baffles within central microchannel 121. In this embodiment, baffles 125 are alternatingly coupled to opposite sides of first central microchannel 121. During operation, baffles 125 can significantly increase the residence time of fluids in the cell culture device 100 and create a non-linear flow path 126 within first central microchannel 121.

In addition, the presence of baffles 125 can induce active mixing performance of contents within first central microchannel 125. In particular embodiments, first central microchannel 125 has a width of up to 3 mm, and a channel height of up to 1 mm. In such embodiments, this low aspect ratio (ratio of height/width approximately 0.33) may tend to collapse porous membrane 140 if baffles 125 were not present. Such a collapse would negatively affect the performance of cell culture device 100. Accordingly, the presence of baffles can successfully sustain the widened micro-scale channels as a spacer to prevent collapsing porous membranes. In certain embodiments, the height of the channels can be modulated.

Figure 4:
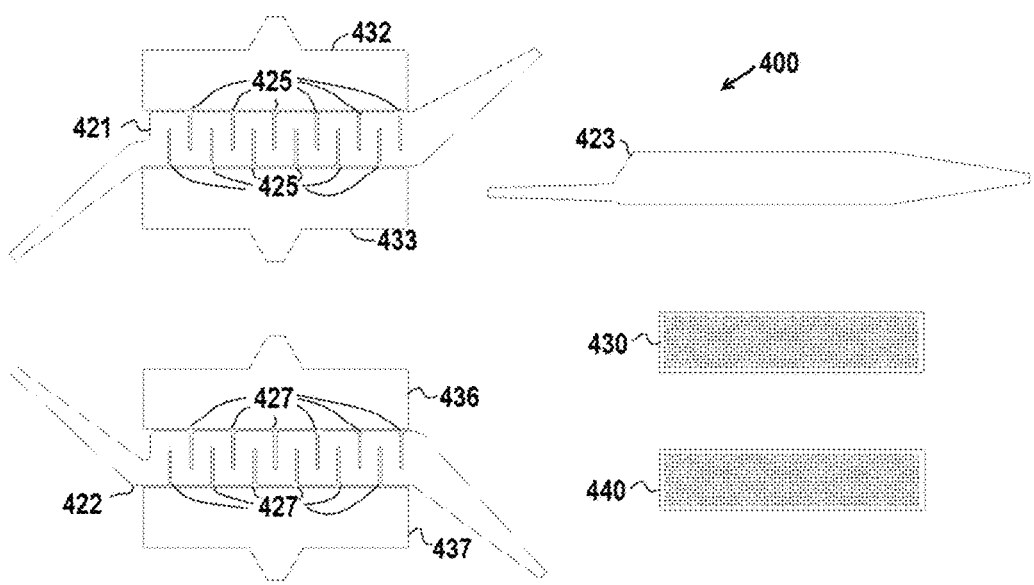
FIG. 4 is an orthogonal view of components of a cell culture device according to exemplary embodiments of the present disclosure.
Figure 5:
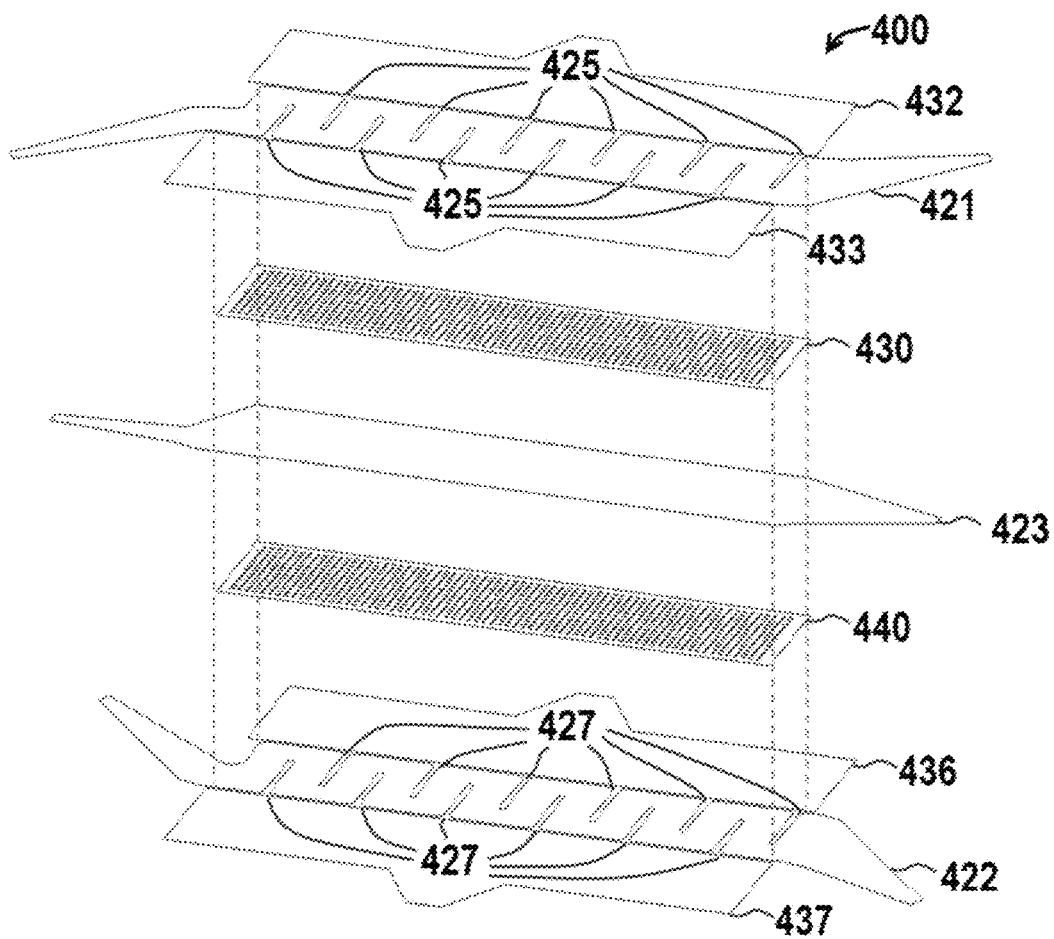
FIG. 5 is a perspective view of the components of the embodiment of FIG. 4.
Figure 6:
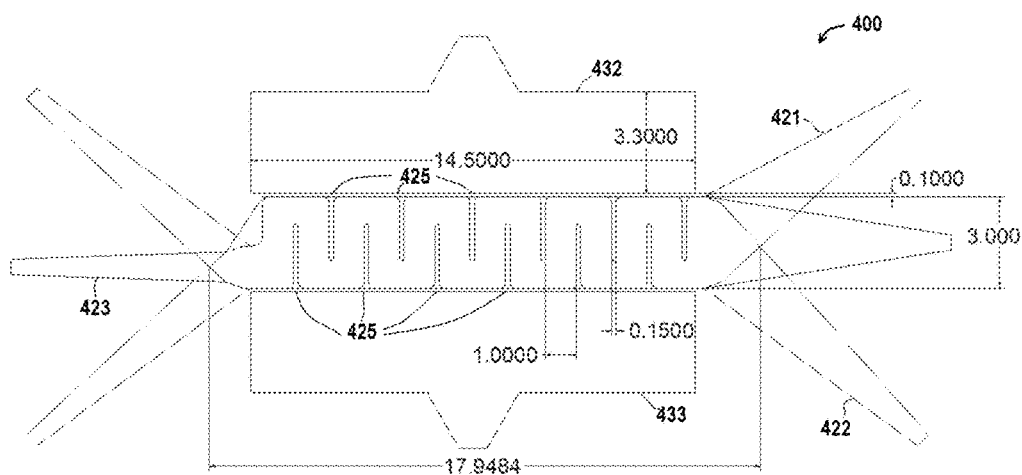
FIG. 6 is an assembly view of the components of the embodiment of FIG. 4.
Figure 7:
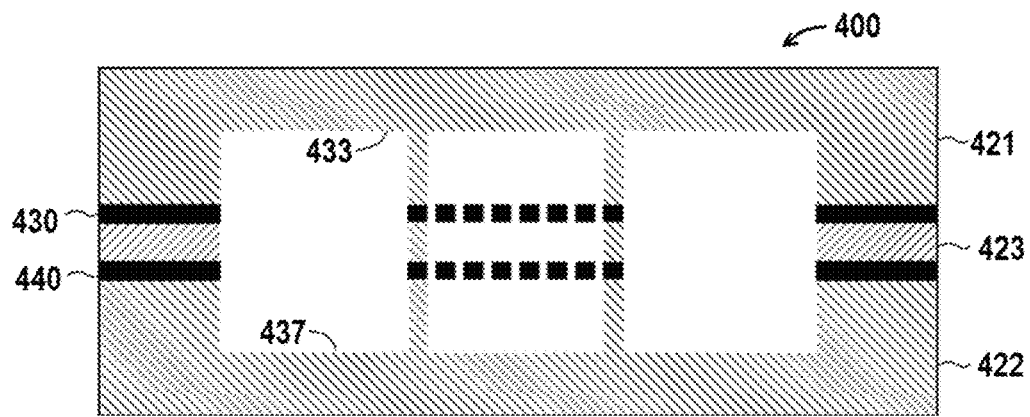
FIG. 7 is a section view of the embodiment of FIG. 4

FIGS. 4-7 provide schematic views of components that can be used in the fabrication of a cell culture device 400. For purposes of clarity, not all components are labeled in each of the figures. As shown in FIG. 4, a first central microchannel 421 (with baffles 425) is disposed between chambers 432 and 433. In this embodiment, a second central microchannel 422 comprises baffles 427 and is disposed between chambers 436 and 437. Cell culture device 400 further comprises a third central microchannel 423 and porous membranes 430 and 440. As shown in FIG. 5, the components can be arranged in a stacked configuration during assembly such that third central microchannel 423 is disposed between porous membranes 430 and 440. First central microchannel 421 (and chambers 432 and 433) can be placed proximal to porous membrane 430 such that porous membrane 430 is disposed between third central microchannel 423 and first central microchannel 421. Similarly, second central microchannel 422 (and chambers 436 and 437) can be placed proximal to porous membrane 440 such that porous membrane 440 is disposed between third central microchannel 423 and second central microchannel 422. FIG. 6 provides a top assembly view of cell culture device 400 with dimensions provided (in millimeters) for certain aspects. It is understood that the dimensions shown in FIG. 6 are merely exemplary of one embodiment of the present disclosure, and that other embodimen55ts may comprise components with different dimensions.

Figure 8:
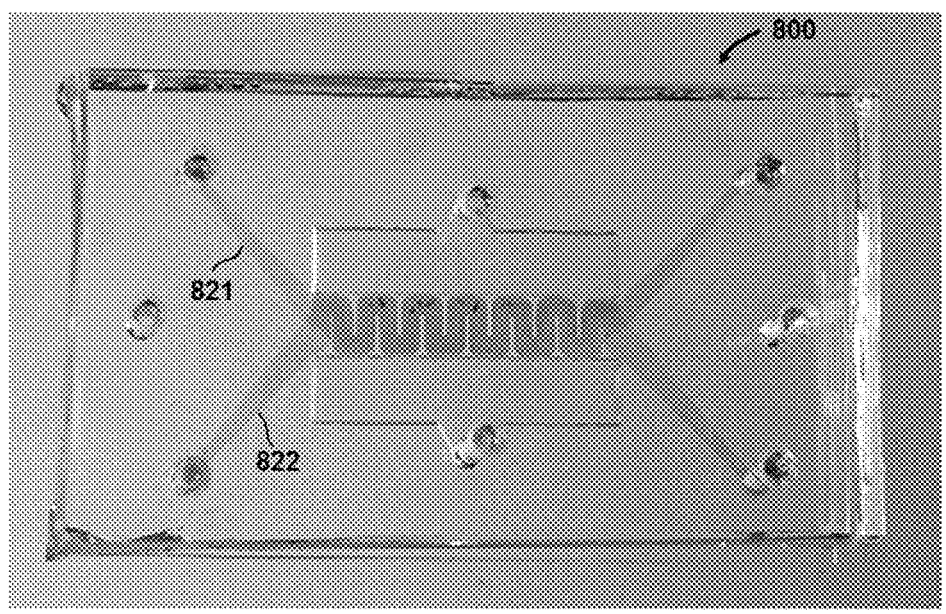
FIG. 8 is a top photographic image of a prototype cell culture device according to exemplary embodiments of the present disclosure.

Referring now to FIG. 8, an embodiment of a device 800 is shown where an upper microchannel 821 is filled with the blue dye, whereas a lower microchannel 822 is filled with the red dye. In this embodiment, device 800 is fabricated using polydimethylsiloxane (PDMS) poured (15:1, w/w ratio of PDMS silicone prepolymer:curing agent) and cured (at 60° C. in a dry oven for at least 6 hours) on the silicon wafer that contains SU-8 patterns of the upper or the lower microchannel. After PDMS patterns are demolded from the silicon wafer, punching holes are made using a biopsy puncher (e.g. 2.0 mm in diameter) and sequentially bonded to the porous PDMS membrane independently prepared in a separate step. For bonding, a handheld corona treater is used to activate the silicone surface, followed by alignment of the upper layer (a top piece with a porous membrane) and the bottom layers. After sufficient curing (e.g. overnight at 80° C. in a dry oven), a complete device with multiple channels is prepared.

Figure 9:
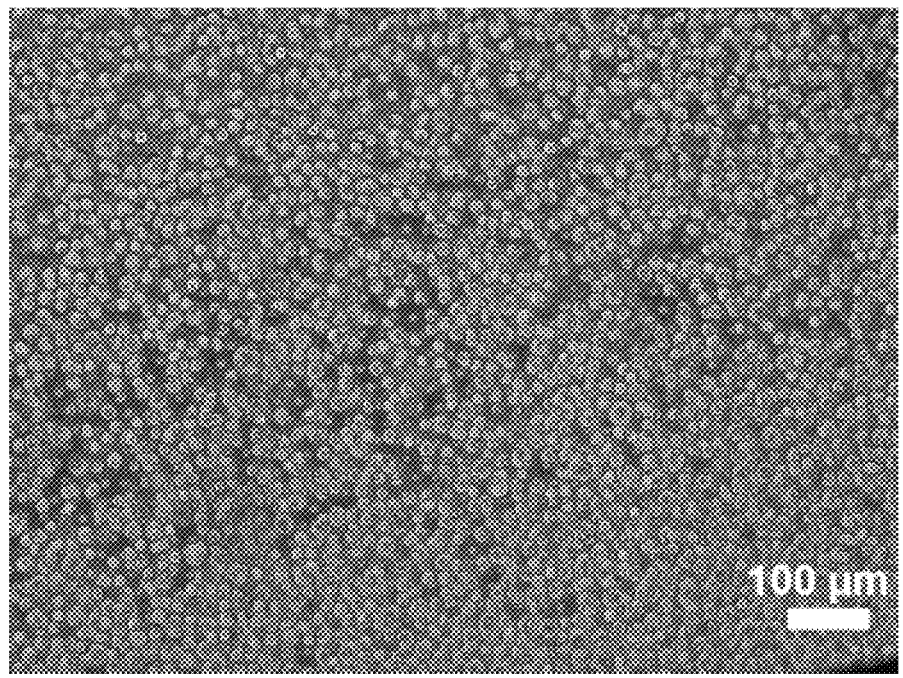
FIG. 9 is a microscopic photographic image of gingival epithelial cells seeded into the upper microchannel of the device of FIG. 8.

Referring now to FIG. 9, a microscopic image is shown of gingival epithelial cells seeded into upper microchannel 821 of device 800 as disclosed herein. In this embodiment, the microchannels are treated with UV and ozone for approximately 40 minutes to activate the surface of channels, followed by a coating step with a coating solution (300 µg/mL Matrigel and 50 µg/mL type I collagen in the serum-free culture medium) at 37° C. for 1 hour. Next, dissociated gingival epithelial cells are introduced into the microchannel at $1.0 \times 10^5$ cells/cm$^2$. The image shown in FIG. 9 was recorded soon after the seeding process.

Figure 10:
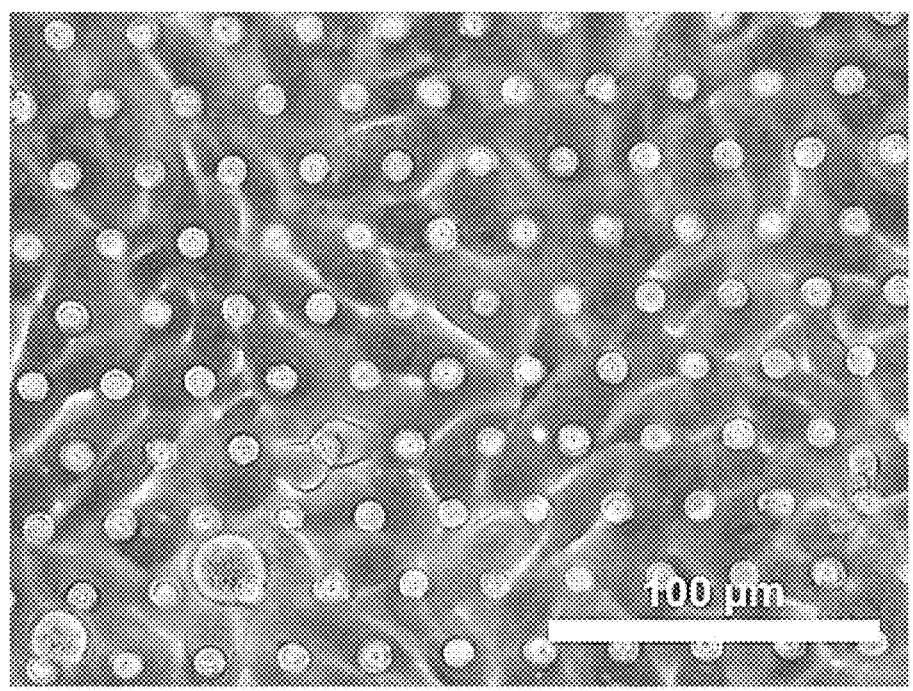
FIG. 10. is a microscopic photographic image of gingival epithelial cells grown in the upper microchannel of the device of FIG. 8.

Referring now to FIG. 10, a microscopic image is shown of gingival epithelial cells grown in upper microchannel 821 of the device 800 at 60 µL/h for 72 hours. As shown in FIG. 10, the cells form tight junctions between the cells.

Examples

The following examples are included to demonstrate exemplary embodiments of the present disclosure. However, those of skill in the art should, in light of the present disclosure, appreciate that many changes can be made in the specific embodiments which are disclosed and still obtain a like or similar result without departing from the spirit and scope of the invention.

Exemplary embodiments of the present disclosure can be applied in many aspects such as the pharmaceutical industry (efficacy and toxicity tests of new drug candidates), clinical researches (disease model, personalized medicine and precision medicine for testing individualized therapeutics, identifying therapeutic targets), biomedical researches (tissue-specific functions by reflecting organ-level responses with molecular-level resolution), or basic research (understanding pathophysiology of human organs under mechanically dynamic conditions).

In particular, exemplary embodiments can be applied in an organ system that has the tissue interface exposed to the environment (e.g. lumen) with reasonable tissue barrier (e.g. tight junction), connective tissue layer that often possesses resident immune system, and the circulating vasculature system to support oxygen and immune cells. Exemplary embodiments provide establishment of a robust host-microbe ecosystem that can support stable steady-state of microbial populations inside the microchannels by modulating fluid shear stress and mechanical deformations, supplying fresh nutrients, and removing microbial wastes (e.g. organic acids) in situ.

Exemplary embodiments of the present disclosure can emulate the micro physiological systems, including the structure (e.g. lumen-mesenchyme-capillary interface) and physiological functions of numerous human organs as described below.

Breast tissue includes a fatty tissue and a glandular tissue (as well as other connective tissues and ligaments) underneath epithelial cells. Ductal carcinoma model can be accomplished in such applications. Nasal cavity applications include an epithelial line and capillary system underneath the tissue. Applications for skin tissue include a layer of epithelial cells in epidermis, capillaries in dermis, and a connective tissue layer composed of collagen and elastin fibers. Tongue applications include the surface stratified squamous epithelium that forms taste buds with connective tissue projections. Esophagus applications have a stratified squamous epithelium, a connective tissue layer (lamina propria), and a smooth muscle layer. In thyroid applications, the glandular epithelium is arranged in follicles lying within a connective tissue stroma, in which blood vessels and lymphatics form rich plexuses around each follicle.

Stomach applications have a line of epithelial cells to protect underlying tissue. Outer layer has gastric pits, mid layer has various different layers of mucosa, submucosa, muscularis and serosa (connective tissue layer) and the bottom layer is visceral peritoneum. Applications for the pancreas have a compound tubular-alveolar gland composed of serous acini (exocrine portion), and islets of Langerhans (endocrine portion). The islets of Langerhans are collections of cell cords separated from the exocrine acinar tissue by a thin connective tissue sheath. Small intestine applications have a monolayer of epithelium on the surface of villi, in which blood capillary and lymph vessel are positioned inside, and connective tissues exist between those layers. Applications for the large intestine (colon) have a similar anatomy with the small intestine (lumen-mesenchyme-capillary) but there are no villi.

For gall bladder applications, epithelium of the gall bladder is tall columnar, with basal nuclei. Under the lamina propria, the muscularis consists of interlacing fascicles of smooth muscle fibers. The connective tissue contains large blood and lymphatic vessels and nerves and it forms fibrosa on the surfaces in contact with the liver. Liver applications comprise hepatocytes (epithelial cells) and fenestrated endothelium lining with space of Disse (connective tissue). In vaginal applications, the vaginal wall underneath the epithelium is made up of connective tissue, muscle tissue, lymph vessels and nerves. Cervix applications have stratified squamous epithelium, connective tissues, and blood vessels. While cervix epithelium near vagina shows squamous structure, epithelium in the canal of the cervix (near uterus) shows columnar structure. Applications for placenta have a villus trophoblast epithelium to make a barrier between fetal and maternal sides, in which fetal part has capillaries, and connective tissues exist between them.

Lung applications have a monolayer of epithelium on the basement membrane, and a layer of endothelium, but there is no connective tissue, found in alveoli or air sacs where gas exchange occurs.

The previously listed examples are merely illustrative applications, and exemplary embodiments may be applied to other human applications and non-human animals including mammal applications having an epithelial barrier, vasculature system, and connective tissues between them. The examples also can be expanded to the natural models that possess the host-microbe ecosystem in a multi-layered compartment in the structure, including insects (e.g. termite's gut) or plants (e.g. fungal-plant interactions).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

PCT Patent Publication WO2012118799
PCT Patent Publication WO2010009307
PCT Patent Publication WO2013086502
Hyun Jung Kim, Hu Li, James J. Collins, and Donald E. Ingber. Contributions of microbiome and mechanical deformation to intestinal bacterial overgrowth and inflammation in a human gut-on-a-chip. *Proc. Natl. Acad. Sci. U.S.A.* 2016 113, E7-E15.
Hyun Jung Kim, Dongeun Huh, Geraldine Hamilton, and Donald E. Ingber. Human Gut-on-a-Chip inhabited by microbial flora that experiences intestinal peristalsis-like motions and flow. Lab Chip 2012, 12, 2165-2174.
Hyun Jung Kim and Donald E. Ingber. Gut-on-a-Chip microenvironment induces human intestinal cells to undergo villus differentiation. Integr. Biol. 2013, 5, 1130-1140.
Dongeun Huh, Hyun Jung Kim, Jacob P. Fraser, Daniel E. Shea, Mohammed Khan, Anthony Bahinski, Geraldine A. Hamilton, and Donald E. Ingber. Microfabrication of Human Organs-on-Chips. Nat. Protoc. 2013. 8, 2135-2157.
Kambez H. Benam, Stephanie Dauth, Bryan Hassell, Anna Herland, Abhishek Jain, Kyung-Jin Jong, Katia Karalis, Hyun Jung Kim, Luke MacQueen, Roza Mahmoodian, Samira Musah, Yu-suke Torisawa, Andries D. van der Meer, Remi Villenave, Moran Yadid, Kevin K. Parker, and Donald E. Ingber. Engineered In Vitro Disease Models. Annu. Rev. Pathol. Mech. Dis. 2015, 10, 195-262.
Mathieu Odijk, Andries D. van der Meer, Daniel Levner, Hyun Jung Kim, Marinke W. van der Helm, Loes I. Segerink, Jean-Phillipe Frimat, Geraldine Hamilton, Donald E. Ingber, and Albert van den Berg. Measuring Direct Current Trans-Epithelial Electrical Resistance in Organ-on-a-Chip Microsystems. Lab Chip 2015, 15, 745-752.
Dongeun Huh, Yu-suke Torisawa, Geraldine A. Hamilton, Hyun Jung Kim, and Donald E. Ingber. Microengineered Physiological Biomimicry: Organs-on-Chips. Lab Chip 2012, 12, 2156-2164.

What is claimed is:

1. A cell culture device comprising:
a body having a central channel disposed therein; and
a first membrane positioned within the central channel and along a plane, the first membrane configured to separate the central channel to form a first central microchannel and a second central microchannel, wherein:
a portion of the first membrane is porous and flexible;
a first fluid is directed through the first central microchannel and a second fluid is directed through the second central microchannel;
the first membrane is configured to support adhesion of a plurality of living cells; and
the first central microchannel comprises a non-linear flow path for the first fluid, wherein:
the first central microchannel comprises a plurality of baffles;
the plurality of baffles are coupled to opposite sides of the first central microchannel;
the plurality of baffles are configured to sustain the first membrane;
wherein living cells are disposed within the central channel;
wherein the living cells are epithelial cells, endothelial cells, myofibroblasts, muscle cells, resident immune cells, macrophages, dendritic cells, mesenchymal cells, neuron cells, smooth muscle cells, or microbial cells;
the first central microchannel has a width of up to 3 mm; and
the first central microchannel has a height of up to 1 mm.

2. The cell culture device of claim 1 further comprising a first chamber and a second chamber, wherein the central channel and the first membrane are disposed between the first chamber and the second chamber.

3. The cell culture device of claim 2 wherein the first chamber and the second chamber are configured to exert a compression force on the first membrane.

4. The cell culture device of claim 2 wherein a pressure within the first chamber and the second chamber can be increased to exert a compression force on the first membrane.

5. The cell culture device of claim 2 wherein the first chamber and the second chamber are configured to exert a tension force on the first membrane.

6. The cell culture device of claim 2 wherein a pressure within the first chamber and the second chamber can be decreased to exert a tension force on the first membrane.

7. The cell culture device of claim 2 further comprising a third chamber, wherein the first membrane is disposed between the third chamber and the second central microchannel.

8. The cell culture device of claim 7 wherein the third chamber is an anaerobic gas chamber and the first and second chambers are pneumatic chambers.

9. The cell culture device of claim 1 wherein the first membrane is coated with a molecule that supports adhesion of a plurality of living cells.

10. The cell culture device of claim 1 further comprising a second membrane positioned within the central channel and along a plane, the second membrane configured to separate the central channel to form a third central microchannel.

11. The cell culture device of claim 10 wherein the first, second and third central microchannels are configured to emulate a structure and physiological functions of a human organ.

12. The cell culture device of claim 10 wherein:
   the third central microchannel comprises a second nonlinear flow path; and
   the third central microchannel comprises a second plurality of baffles.

* * * * *